United States Patent [19]
Login et al.

[11] Patent Number: 5,093,031
[45] Date of Patent: Mar. 3, 1992

[54] SURFACE ACTIVE LACTAMS

[75] Inventors: Robert B. Login, Oakland; Ratan K. Chaudhuri, Butler; Rama K. Haldar, Randolph; Mohamed M. Hashem, Wayne; Michael W. Helioff, Westfield; David J. Tracy, Lincoln Park, all of N.J.

[73] Assignee: ISP Investments Inc., Wilmington, Del.

[21] Appl. No.: 257,596

[22] Filed: Oct. 14, 1988

Related U.S. Application Data

[63] Continuation-in-part of Ser. No. 879,776, Jun. 27, 1986, abandoned, and a continuation-in-part of Ser. No. 13,760, Feb. 12, 1987, abandoned.

[51] Int. Cl.$^5$ .............. B01F 17/16; C07D 207/00; C07D 223/10
[52] U.S. Cl. .............................. 252/357; 540/485; 540/529; 546/243; 548/401; 548/529; 548/530
[58] Field of Search .............. 548/401, 543, 279, 530; 546/8, 9, 243, 211; 540/486, 485, 531, 529; 252/351, 357

[56] References Cited

PUBLICATIONS

*Chemical Abstract*, vol. 84, #16587u, 1976 Denzinger et al., "Water–Insoluble Slightly–Swelling N-Vinyl Lactam Polymers with Improved Adsorption".
*Chemical Abstract*, vol. 80, #41385z, 1974, Nakagaki et al., "Phase Seperation and Surface Tension of ag.HCl Acid Solution of N–Dodecyl-2-Pyrrolidone".
*Chemical Abstract*, vol. 99, No. 107533x, Ranbom, 1983, "Hydrogen Peroxide".

*Primary Examiner*—C. Warren Ivy
*Assistant Examiner*—Raymond Covington
*Attorney, Agent, or Firm*—McAulay Fisher Nissen Goldberg & Kiel

[57] ABSTRACT

The invention relates to properties and uses of N-hydrocarbon substituted lactams, particularly N-alkyl substituted lactams having the formula

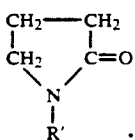

wherein R' is a hydrophobic radical such as linear or branched chain alkyl group containing from 8 to 27 carbon atoms, most preferably micelle forming pyrrolidones having 12 to 16 carbon atoms in the R' group. The invention particularly relates to the uses of the N-hydrocarbon substituted lactams which involve surfactant properties, such as solubility, wetting, viscosity building, emulsifying and/or complexing properties.

2 Claims, 4 Drawing Sheets

SURFACE ACTIVE LACTAMS

CROSS REFERENCE TO RELATED APPLICATIONS

This is a continuation-in-part of co-pending application Ser. No. 879,776, filed June 27, 1986, abandoned, and application Ser. No. 013,760, filed Feb. 12, 1987, abandoned, both entitled "SURFACE ACTIVE LACTAMS".

BACKGROUND OF THE INVENTION

N-lower alkyl pyrrolidones have found wide commercial acceptance as non-toxic, aprotic chemical solvents. However, absence of hydrophobic-lipophobic balance in these molecules, as in the case of N-methyl pyrrolidone, prevents micellular formation; consequently, they possess no significant aqueous surfactant properties. Linear amine oxides are known to possess high surfactant activity; however these compounds are not stable at high temperatures and cannot be employed in metal working or high temperature fiber processing.

Accordingly, it is an object of the present invention to overcome the above deficiencies by providing improved surfactant-complexant agents which are readily obtained in an inexpensive and commercially feasible manner.

Another object of this invention is to provide a group of compounds having excellent surfactant and complexing properties.

Another object is to provide a group of compounds having viscosity building and wetting properties.

Still another object is to provide specialized processes for using micelle forming pyrrolidones and to provide novel compounds resulting from such processes.

These and other objects of the invention will become apparent from the following description and disclosure.

SUMMARY OF THE INVENTION

According to this invention there is provided uses for a distinctive group of N-hydrocarbon substituted lactams having unusual properties and defined by the formula

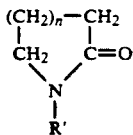   A.

wherein n is an integer having a value of from 1 to 3 and R' is a hydrophobic radical selected from the group consisting of a linear, branched chain or cyclic alkyl radical containing from 8 to 22 carbon atoms; a naphthyl or alkyl substituted naphthyl radical containing from 10 to 26 carbon atoms and an alkylphenyl or phenylalkyl radical containing from 9 to 26 carbon atoms; of which a restricted group of N-$C_{12}$ to $C_{22}$ alkyl pyrrolidones are capable of forming micelles in neutral, basic or acidic aqueous media and or have a critical micelle concentration of between about $1 \times 10^{-3}$ and about $5 \times 10^{-5}$ moles per liter. Of the above lactam surfactants, the N-alkyl pyrrolidones containing 12 to 16 carbon atoms in the N-alkyl group are preferred and, of these, N-$C_{12}$ to $C_{14}$ alkylpyrrolidones having a critical micelle concentration less than $2 \times 10^{-2}$ moles per liter are most preferred.

It is intended to include lactams wherein one of the hydrogen atoms bonded to a carbon atom member of the heterocyclic ring can be substituted with methyl or ethyl.

DESCRIPTION OF THE PREFERRED EMBODIMENT

Figure 1:
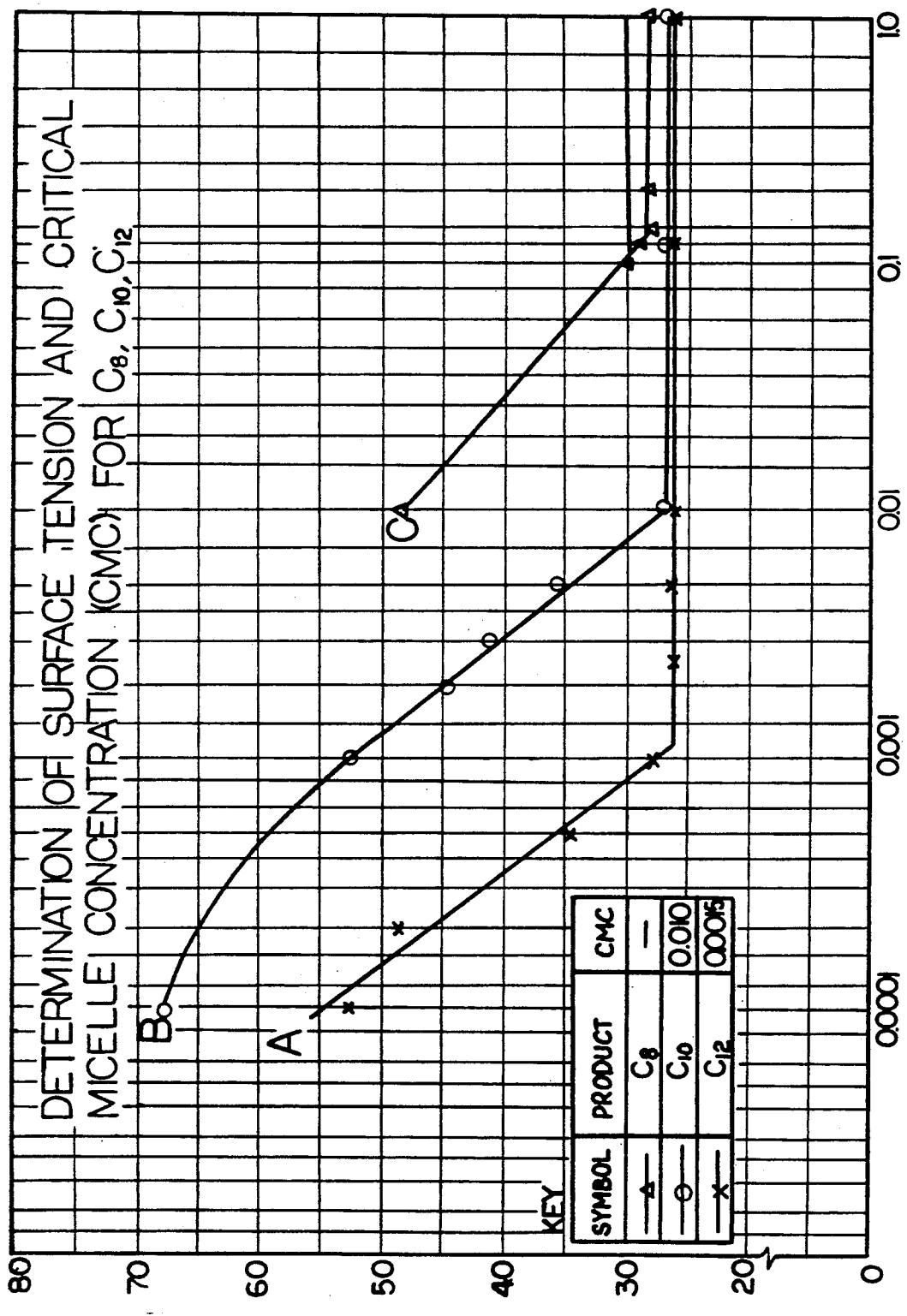
FIG. 1 is a graph depicting the variation and surface tension with concentration for various N-alkyl-2-pyrrolidones.

The cyclic hydrophilic moiety of the compounds herein defined is an important factor in maximizing their efficiency by concentrating the molecule, and thus the surfactant activity, at the interface of and minimizing the solubility of the molecule in liquid phases. Such surfactant properties are unexpected since the compounds lack the polyalkoxy groups commonly associated with conventional nonionic surfactants. By way of comparison, N-dodecyl-2-pyrrolidone, exhibits surfactant properties equivalent to a lauryl alcohol containing five moles of ethoxylate, i.e. $C_{12}H_{25}$-$(CH_2CH_2O)_5H$, a known commercial non-ionic surfactant.

Of the present lactams, the pyrrolidones having R' substituents containing less than 12 carbon atoms do not have hydrophobic groups of a length sufficient to form micelles in water. Those having R' alkyl substituents of hexadecyl and above tend to exhibit some imbalance such that the hydrophilic pyrrolidone or caprolactam moiety is less dominating than the hydrophobic character of the alkyl group. However, these higher molecular weight compounds can provide surfactant properties in non-aqueous systems and are valuable wetting agents in applications involving solid substrates.

The structure of the present lactams provides a key to their unique properties, which make them useful for certain applications.

Specifically, the present lactams possess excellent spot, stain and soil releasing properties. They have the ability to retain fragrances in perfumes. They also display anti-stat, anti-block and lubricant properties and are complexing agents. Also, it has been found that they are excellent thickening agents for quaternized compounds, phosphate esters, mineral acids and anionic sulfates and generally combine surfactant properties with complexability which makes them useful as dye penetrating, and dye exhaust agents as well as desirable detergent additives.

The highly polar and hydrophilic pyrrolidone moiety exhibits several resonance forms, i.e.

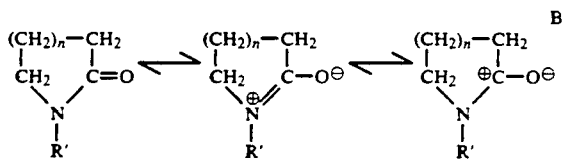
B.

The existence of such multiple resonance states contributes to the high dipole moment of about 4 debye, possessed by these lactams. A high dipole moment is an important property, conferring the ability of these molecules to assume multiple resonance forms which promotes their tendency to complex or interact with many chemical groups. For example, the ability of these compounds to interact with anionic moieties, e.g. sulfate groups, quaternized groups, mineral acids, phosphate esters, etc. is beneficial in thickening formulations and in reducing skin irritability of various medicinal creams and lotions containing such or similar groups.

The above lactam products having a molecular weight of from about 180 to about 450 are conveniently prepared by several known processes including the reaction between a lactone having the formula

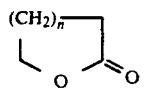

wherein n is as defined above, and an amine having the formula $R'-NH_2$ wherein $R'$ is as defined above. The amine reactant having the formula $R'-NH_2$ includes alkylamines having from 7 to 20 carbon atoms; naphthyl or alkylnapthyl amines having from 10 to 26 carbon atoms; alkylphenyl or phenylalkyl amines having from 9 to 26 carbon atoms; amines derived from natural products, such as coconut amines or tallow amines and distilled cuts or hydrogenated derivatives of such fatty amines. Also, mixtures of amine reactants can be used in the process for preparing the present compounds. Such mixtures can include cyclic, linear and branched chain amino species having an alkyl or other organic substituent of the same or different molecular weight. In the present process the amine and lactone reactants, combined in a mole ratio of from about 1:1 to about 1:5, are reacted under conditions of constant agitation, at a temperature between about 00° C. and about 350° C. under a pressure of from atmospheric to about 650 psig for a period of from about 1 to about 15 hours; preferably at 250° C. to 300° C. under an initial ambient pressure for a period of from 5 to 10 hours. The resulting lactam product is recovered and purified by distillation or by any other convenient recovery process.

The N-alkyl lactam products having 11 to 14 carbon atoms are clear, water white liquids, at room temperature; whereas those having 16 or more carbon atoms are solids. These lactams have a neutral or slightly basic pH, a surface tension between about 25 and about 35 dynes/cm as a 0.1% water solution and a viscosity of from about 6 to about 30 cps at 25° C.

Generally, the $C_8$ to $C_{14}$ alkyl lactams display primarily surfactant properties; whereas the $C_{16}$ to $C_{22}$ alkyl species are primarily complexing agents; although some degree of surfactants and complexing capability exists in all of the present species.

More particularly, the N-$C_{12}$ to $C_{22}$ alkyl pyrrolidones are capable of producing micelles at a critical molar micelle concentration between $1 \times 10^{-3}$ and $1 \times 10^{-5}$, whereas pyrrolidones having an N-alkyl substituent of $C_{10}$ or less are incapable of micellular formation by themselves. They readily form mixed micelles with every other type of surfactant—that is why they can thicken other micellular systems.

The decyl and lower N-alkyl pyrrolidone species fail to form micelles since they have insufficient hydrophobicity to counteract the action of the pyrrolidone groups in the interactions (a) and (b)

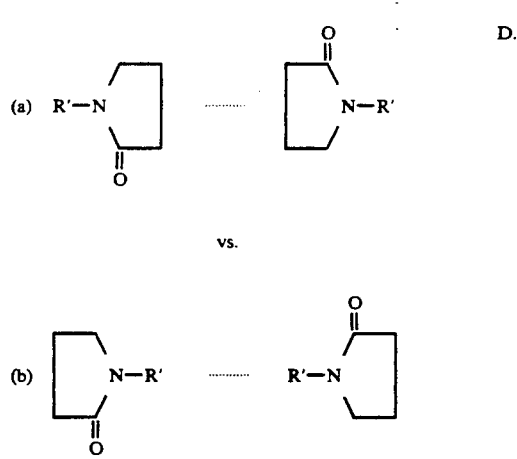
D.

The decyl, octyl and lower alkyl species are governed by interaction (a) which predominates and the resulting dimer is insoluble for the reason that the R' groups are exposed in terminal positions of the interacted molecules thus reducing the hydration of the pyrrolidone moieties. Conversely, for longer chain R' groups, interaction (b) is the governing interaction and stable micelles, as depicted in E. form where interaction occurs because the R' groups are hydrophobic.

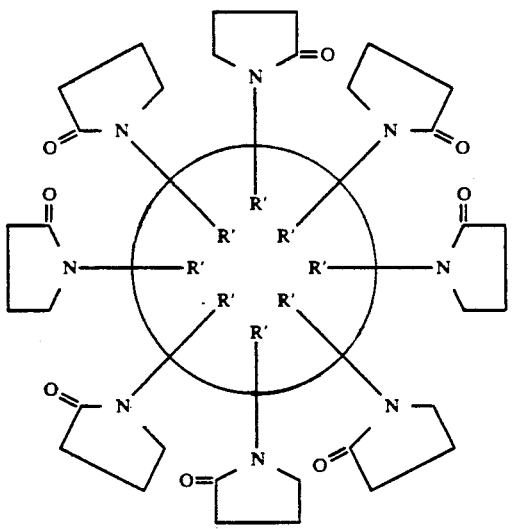

E.

The micellular structure of the N-$C_{12}$ to $C_{22}$ alkyl pyrrolidones provide unique complexing capability with compounds, such as, for example, compounds having an acidic hydrogen atom, e.g. phenolic compounds, compounds having a polarizable structure, halogens, mercaptans, ureas and metal oxides, since such compounds complex with the micelle rather than with a single mole of the pyrrolidone and are either contained within the micelle or interposed between the pyrrolidone moieties protruding from the micelle boundary. Accordingly, the micelle is capable of complexing with larger amounts of the compound than would be dictated from a molar level.

The maximum surface concentration of the present surfactants at equilibrium above the critical micelle concentration is exceptionally high, i.e., between about 2 moles/cm $\times 10^{-10}$ and about 5 moles/cm $\times 10^{-10}$. It is believed that the monodisperse nature of the hydrophobe and hydrophile moieties of the these surfactants contribute to the high surface concentrations by maximizing entropy of packing, particularly in the case of the N-dodecyl-2- pyrrolidone and the N-tetradecyl-2-pyrrolidone species which exhibit essentially balanced hydrophobe/hydrophobe and hydrophile/hydrophile interactions at the liquid interface. Longer R groups, e.g., $C_{18}$ or more may form polymicelles so as to avoid packing due to steric effects.

The present group of lactams also exhibit a unique and heretofore unrealized combination of properties, suitable for increasing rates of solubilization for solids in a liquid medium in which they are normally insoluble. Many drugs having little or no solubility in water are orally administered in the form of pills, tablets or capsules. Examples of such drugs include hydrochlorotriazide, chlorothiazide, griseofulvin, progesterone, phenyl butazone, and sulfathiazole.

Drugs are usually administered as a complex formulation. In particular, drug compositions often contain surfactants which can influence the de-aggregation and dissolution of an active ingredient. They can also control the rate of precipitation of a drug which is administered in solution form by increasing the membrane permeability and membrane integrity. Surfactants may also influence the binding of the drug to a receptor site. Water soluble drugs will not bind, whereas water insoluble drugs will interact with surfactant molecules. Thus, high concentrations of surfactants are likely to affect the lipophilic and hydrophobic drugs in differing degrees.

Release of poorly soluble drugs from tablets and capsules for oral use can be increased by the presence of surfactants, which, as noted, may decrease the aggregation of the drug particles and in turn increase the area of the particles available for dissolution. Surface tension lowering may also be a factor in aiding the penetration of water into the drug mass. Such a wetting effect is generally operative at low concentrations. Above the Critical Micelle Concentration (CMC), the increase in the saturation solubility in the drugs by solubilization of the surfactant micelles can result in more rapid rates of drug solution. Where dissolution is the rate limiting step in the absorption process as it is with many poorly soluble drugs, an increase in rate of solution will increase the rate of drug entry into the blood and may affect peak blood levels. Certain N-alkyl lactams, such as, N-dodecyl-2-pyrrolidone have been used to enhance the release of drugs, such as, salicylic acid and indomethacin from ointment bases. [See M. Shizozaki et. al., Yakuzaigaku, 42, 10–16 (1982); CA 97:389 (1982)]. Also see U.S. Pat. Nos. (3,991,203—4,039,664—4,316,893—4,405,616—4,415,563—4,423,040—4,424,210—4,444,762—4,557,934) and Japanese patent (6133,128).

These drugs may be formulated with non-pyrrolidonic anionic surfactants, such as, sodium lauryl sulfate, dioctyl sodium sulfosuccinate or non-ionic surfactants, such as, polyoxyethylene (20) sorbitan monoleate (Tween 80) or polyoxyethylene (23) lauryl ether. Polyoxyethylene based non-ionic surfactants may contain dioxane and, in the case of those derived from fatty amines, such as, polyoxyethylated (5) tallow amine, nitrosoamines which are well known carcinogens. The present lactams, besides their ability to diminish aggregation of drug particles and increasing the area available for dissolution, are free of dioxane and nitrosoamine contaminants and the purity of these non-alkoxylated compounds is more readily assured since they are not subject to variations of extraneous by-product contamination or degree of alkylene oxide polymerization. Unlike sodium lauryl sulfate, the present pyrrolidones are non-irritating and do not react with acidic drugs or pharmaceutical excipients. Additionally, the present lactams possess the ability to solubilize a drug as well as the capability of lowering surface tension to permit water and digestive fluid penetration into the drug mass, thus increasing the rate of drug entry into the blood stream. In certain cases, where dissolution is the rate-limiting step in the absorption process, these lactams in many instances actually increase the normal peak saturation levels in the blood for a particular drug.

In particular, we have discovered that by essentially the mere compounding of the N-$C_8$ to $C_{14}$ alkyl pyrrolidones with an insoluble organic compound and, in particular, a pharmaceutically active compound, the rate of dissolution of such compounds can be substantially enhanced. Additionally, we have discovered that it is only those N-alkyl pyrrolidones having from 8 to 14 carbon atoms in the N-alkyl group which produce this result.

Moreover, with the present invention, it is unnecessary to chemically modify the compound in any way, thus preserving, intact, its pharmaceutical activity. This can be accomplished by forming a physical blend of the N-$C_8$ to $C_{14}$ alkyl pyrrolidone with the pharmaceutically active ingredient along with any other conventional adjuvants. Typically, a solution of the pyrrolidone is blended with the insoluble pharmaceutical, the solvent removed and the dry formulation formed into the appropriate dosage form, i.e., tablets, capsules, and the like. A variety of correctional solvents can be used for this purpose. It is only necessary that they be pharmaceutically acceptable. These include, for example, water and alcolhols, e.g., ehtanol, 2-propanol.

Additionally, the pyrrolidone and the insoluble compound can be dry blended without the use of a solvent. This would typically be effected using a ball mill or other conventional device of this type. It is only necessary that intimate mixing or blending of the two ingredients be achieved.

A particularly beneficial property of the instant N-$C_{12}$ to $C_{22}$ alkyl pyrrolidones is their complexing ability, in which the complexed active compound is positioned in the micelle or on the micelle surface. The pyrrolidone containing molecules in turn migrate to the surface of a bulk solution forming a monomolecular or dimolecular film thereon; thus concentrating the chemical which has been complexed at the solution-substrate interface or within the micellular structure. Spacial concentration of the active ingredient at the liquid surface or penetration beyond the water soluble pyrrolidone micelle surface provides more efficient contact between the complexed chemical and the substrate, thus permitting the efficient use of an active ingredient to perform its intended function. The lower concentration of an active ingredient such as a drug having toxic properties, can result in lowering toxicity and alleviating undesirable side effects. The advantage of complexible compounds taken within the micellular structure is that larger amounts can be taken up than could be normally achieved from a mole on mole basis complexing. Because the present compounds tend to concentrate the active ingredient at or near the surface of its micellular structure, smaller dosages of the active ingredient can be employed and more efficiently utilized. Accordingly, the present lactams serve as valuable adjuvants for active ingredients in liquid solution which are applied to a substrate.

The complexing capability of the present products involves a wide range of organic and inorganic compounds and includes compounds containing a phenolic group, a mercapto group, an acidic hydrogen, metal oxides compounds, metal salts, halogens and polarizable compounds. More specifically, these compounds include mineral acids, such as, the hydrogen halides, particularly hydrochloric acid, sulfuric, nitric, phosphoric acids, etc., organic acids, such as, chloroacetic, acetic, formic, etc., phenolics, such as, vanillin, phenol, resorcinol, phenyl mercuric hydroxide etc. metal salts, such as, $SnI_2$, $BiC_6H_5O_7$, $SbF_3$, etc., halogens such as $I_2$ $Br_2$ and $Cl_2$ and polarizable compounds, such as, $I_2$, $HI_3$, and resonant structures, i.e., dyestuffs and fluorescent dyes and perfumary materials, etc. The inventive compounds also complex with mercaptans, such as, thioglycolates, urea and urea derivatives and odor forming components of human perspiration to mask or remove odor and stains caused by these components.

Additionally, the inventive compounds control objectionable odors emanating from metal treating and slaughter house operations as well as household odors on rugs, furniture, clothing, or encountered in pet environments, veterinary sites. The present surfactants also complex with odor forming bodies in animal and human wastes containing, e.g., mercaptans, urea, tars, nicotine, molds, and other odor causing chemicals.

The present N-alkylpyrrolidones are excellent clarifying agents for beverages, particularly beer and wines, which contain phenolic and other impurities. Removal of contaminants results in a product having improved clarity, taste and color. Beverage impurities can be removed by several methods. For example, water soluble pyrrolidones of this invention, also soluble in the beverage, are complexed with the phenolic impurities at a temperature below their respective cloud points. When the beverage is heated above the cloud point of the lactam employed, the resulting complexed impurities, e.g., polyphenols/lactam, are separated and thus removed. This method of clarification is beneficially employed using N-alkyl $C_{10}$ to $C_{14}$ pyrrolidones. Water insoluble N-alkyl lactams of this invention, e.g., N-hexadecyl, N-octadecyl and N-tallow pyrrolidones are also useful and are employed to extract impurities by intimately mixing the lactam and beverage. The phenolic impurities, mainly polyphenols, preferentially complex with the heterocyclic ring of the water insoluble lactam and are then removed by filtration. Still further the complexability and high heat stability of the present lactams makes them valuable decontaminating agents for industrial wastes.

The above surfactant and complexing properties of the present lactams combine to provide products of the present invention which are useful (1) in the solubilization of insoluble compounds, (2) as anti-static agents and slip and antiblock agents for incorporation of components into plastic films to decrease the coefficient of friction, (3) as hydrolysis resistant solvents and auxiliaries for use in either acid or caustic environments, (4) as agents for retaining fragrance odors in perfume, (5) as thickeners for quaternized compounds, phosphate esters, and anionic sulfates, (6) as viscosity builders to form gels and pastes, (7) as thickeners for mineral acids to prevent splattering, (8) as dye penetrating and dye exhaust agents, (9) as beverage clarifiers, particularly beer and wine clarifiers, (10) as stain and spot removers for textiles, (11) as surfactants for wettable powders and detergents, (12) as detergent surfactants, (13) as agents for increasing the rate of dissolution of normally insoluble tablets or pills, (14) as detoxifying agents and many other uses which will become apparent from the present description and disclosure.

The lactams of this invention are soluble in most organic solvents including glycerin, acetone, lower molecular weight alcohols, toluene, polyethylene glycols, polypropylene glycols, xylene, heptane, methylene chloride, perhalogenated lower molecular weight hydrocarbons, paraffin oil, Stoddard solvent, etc., and are compatible with all classes of surfactants under varying pH conditions. The water dispersibility properties of the $C_{10}$ to $C_{14}$ alkyl species seems to contravert the generally accepted chemical behavior of hydrocarbon compounds. One would expect that as the alkyl chain length increases, the compound would become more hydrophobic. Instead, it is now discovered that while N-octyl pyrrolidone is substantially insoluble in water, the N-decyl species shows partial solubility and the N-dodecyl and N-tetradecyl pyrrolidones are completely water dispersible. Water insolubility is again evidenced in the pyrrolidones having alkyl groups of 16 or more carbon atoms, for the reasons explained above. However, blends of higher alkyl species with the $C_8$ to $C_{14}$ alkyl species are water dispersible by algebraic summation of the individual contributions of the respective alkyl and pyrrolidone moieties to the hydrophobic/hydrophilic balance. Also a hydrotrope or a mineral acid electrolyte, e.g., a hydrogen halide such as HCl, sulfuric acid, phosphoric acid, xylene sulfonate, toluene sulfonate, cumene sulfonate, an alcohol, a short chain fatty acid, in low level concentration, aids in improving water dispersibility of the N-$C_8$ to $C_{10}$ alkyl pyrrolidones since they are readily solubilized in aqueous solutions of pH 6 or less.

The present compounds impart anti-static and softening properties to fabrics during a laundry drying or washing cycle. It is discovered that residual anti-static protection is provided even when the present surfactants are added only in the washing cycle. Accordingly, these pyrrolidones can be added to a detergent formulation or can be applied directly to a fabric to coat fibers or to a cellulosic material, e.g., as an anti-static spray, for rugs or clothing or can be used as paper coated strips which are added to a dryer. Soil release and anti-soil deposition on fabrics is also imparted when the fabrics are coated, washed or otherwise contacted with the pyrrolidones of this invention. Instant products also can be applied to printing rollers or any equipment where slippage, friction or other factors build-up a considerable electrostatic charge as, for example, in electronic equipment or equipment used for the manufacture of certain plastics. Additionally, the excellent thermal stability of the present lactams makes them useful as high temperature anti-static agents and permits their formulation into molten plastics, such as, polyethylene, polypropylene, nylon, mylar, etc., before extrusion without any degradation of the plastic. In such oleophilic matrices, the hydrophilic pyrrolidone migrates to the plastic surface and acts as an antistat and anti-blocking agent.

The complexing properties of the N-$C_{12}$ to $C_{22}$ alkyl pyrrolidones makes them particularly effective as biocidal washing agents employed for hospital, household or industrial use. A particular application would involve the micellular complex formed between iodine and these pyrrolidones as an effective antiseptic solution which can be used as such, e.g., as a spray, or can be added to a detergent solution to provide or enhance germicidal properties. Also, such complexes of the higher molecular pyrrolidones of $C_{14}$-$C_{22}$ alkyl species, having higher viscosity, can be applied to wounds as a cream or as a flexible antiseptic bandage or can be formulated into other compositions to enhance viscosity.

Because of their excellent wetting, fixative and complexing properties the $C_8$ to $C_{22}$ alkyl-2-pyrrolidones are beneficially incorporated in formulations for perfume, as a fixing agent to retain the odor producing agent on the surface of the skin where applied. Biocidal solutions using complexes of the present pyrrolidones with various drugs can be used in veterinary medications or as disinfectant washing solutions, such as a wash for range cattle to kill incipient bacteria while providing residual inhibition of future infections from ticks and other pests.

The excellent wetting properties of the instant lactams recommends them as outstanding surfactants for use in concentrate formulations of wettable powders, which are subsequently diluted with water to form aqueous suspensions suitably employed as sprays. These suspensions which include the lactams in the active concentrate formulation are distinguished by significantly improved stability over extended periods. The method for preparing the concentrate involves blending the active component, preferably having a particle size less than 25 micrometers, with an inert carrier, a dispersing agent to prevent flocculation and the lactam wetting agent to facilitate the suspension of particles. The blend is generally milled, e.g., on a fly cutter mill operated at about 20,000 rpm, at ambient temperature for a period of from about 0.5 to about 5 minutes. This operation provides a wettable powder concentrate having a suspensibility greater than 75% and a wetting time of less than 3 seconds. Suitable fillers for the concentrate include clays, talc, silica powder, bentonite, and diatomaceous earth. The blends of anionic dispersing agent and the nonionic lactam with the wettable powder and filler ensures good storage stability and improves suspension properties upon dilution in the field. The present lactams are highly compatible with anionic dispersants commonly employed, such as Igepon T-77 (a sodium salt of fatty acid amide sulfonate), Blancol (the sodium salt of sulfonated naphthaleneformaldehyde condensate) and Marasperse N (a lignosulfonate). The lactams also guarantee good formulation and tank mixing capability with the most common active ingredients.

Certain synthetic fibers, for example polyesters, nylons, orlon and fiber blends, are difficult to dye because they provide insufficient ionic sites on which the dye can attack. Accordingly, dying of such fibers or fabrics is usually effected with disperse dyes which require no complexing function for color development. However, one objection to this type of dying is that the product does not possess high color fastness. The present nonionic surfactant/complexing lactams which lower surface tension and interact with both anionic and cationic substances, promote acceptance of non-disperse dyes such as, for example, the acid dyes, cyanine dyes, anthraquinone dyes, quinoline dyes and thiazole dyes on relatively difficult dyeable materials while simultaneously providing faster release and higher exhaust of the dye from carrier and onto the textile substrate.

The pyrrolidone products of this invention are also excellent viscosity builders, the $C_{12-14}$ species being outstanding. Accordingly, these pyrrolidones can be added to liquid formulations to provide gels or pastes. This application is extremely desirable where noxious or skin irritating liquid chemicals of low viscosity are employed. For example, gels or pastes of strong acids can be provided to eliminate splattering or fuming and more viscous compositions containing the active chemical can be applied for retention on vertical surfaces, e.g., to effect rust removal.

Because of their surfactant properties, the present pyrrolidones also hinder the formation of hard water precipitates. Still further these products, which possess high plastic substantivity, provide internal and external lubricity to polymeric products such as those which are made from or contain polystyrene, polyethylene, polypropylene, polyvinyl chloride, nylon, cellulose acetate, polyvinyl acetate, phenolic resins, polyvinyl pyrrolidone, etc. Surface lubricating effects on metals have also been noted. Selection of individual N-alkyl pyrrolidones of the $C_8$-$C_{22}$ alkyl species or combinations thereof provide the effects mentioned above in finished formulations and other effects which will become apparent from the present disclosure.

Still another field in which the present lactams find application is in dry cleaning. Dry cleaning solvents generally fall into two categories, namely the petroleum solvents and the halogenated solvents which include Stoddard solvent (a petroleum distillate between gasoline and kerosene), carbon tetrachloride, trichloroethylene, perchloroethylene, fluorinated hydrocarbons, 104F solvent, etc. Although these solvents are satisfactory for the removal of fatty type soils, many water soluble spots and stains, e.g., tea, fruit, wine, ink and beer stains, are not removed. However, when the present solvent soluble lactams are added to the formulation, such water insoluble stains are easily removed. These lactams, particularly the pyrrolidones herein defined, complex with acidic molecules, labile protons, polarizable molecules and color forming components. Thus, they can solubilize water in the dry cleaning formulation thus assisting in removing water soluble stains. They also complex with odor causing components in human perspiration, this minimizing or eliminating odor retained in clothing including polyester fabrics. The present lactams are also efficacious in removing soil and stains when added to a standard laundry detergent. The effective amount of lactam incorporated in dry cleaning or laundry detergents for the above purposes is generally at least 1% by weight, preferably between about 2% and 50% by weight of the total formulation. As a specific spot and stain remover, however, the present lactams, particularly the pyrrolidones, can be used individually or in admixture in 100% concentration with no additive. For effective stain removal, usually an amount which wets the entire stain will suffice to give desired results.

In view of the diverse fields of application in which the present compounds are beneficially employed, it will be appreciated that widely varying amounts of these compounds can be used to fulfill their requirements and other functions which may become obvious. Generally, between 100% and about 0.001% of these surfactants, depending upon their use as a compound per se or as an additive to an existing formulation, will become apparent. More specifically, when one or more of the present products is used as an anti-static spray or stain remover, up to 100% of the active ingredient can be the present pyrrolidone or a blend thereof. On the other hand, when the present product is an additive in a laundry, dishwashing or cosmetic formulation, its concentration can be as low as 0.001%. For complexing, the concentration of pyrrolidone depends entirely on the chemical nature of the compound and the amount of active component one desires to incorporate. Generally, the amount employed is within the mole ration range of between about 0.5:1 and about 99:1 lactam to active component and an amount at least sufficient to retain the beneficial characteristics of the lactam but not more than the amount needed to preserve the effect of the active component being complexed.

As viscosity builders, up to 80% of the product may be present in the formulation. Most often, the amount of lactam product employed is the same or somewhat less than that amount used for agents having a similar property in the same field of application.

Having thus described the invention, reference is now had to the following examples which set forth preferred embodiments but which are not to be construed as limiting to the scope of the invention as more broadly described above and as set forth in the appended claims. It should be recognized that these examples are presented only to more specifically describe the invention, to exemplify preferred embodiments and to provide representative examples of use from which other uses and applications will become apparent.

EXAMPLE I

Into a stainless steel autoclave was introduced dodecyl (2342 g) and butyrolactone (1704 g) in a mole ratio of about 1:1.1. The autoclave was sealed and 100 psig of nitrogen applied and the contents heated to 275° C. and held for 8 hours during which time the reaction mixture was agitated and the pressure increased from atmospheric to about 480 psig. The reaction produced a liquid product which recovered from the autoclave and distilled to produce 99.2% pure clear water white liquid N-dodecyl-2-pyrrolidone in a yield of 99% and having a cloud point of 15°-19° C. (10% water solution), a boiling point of 145° C. at 0.2 mm of Hg, a viscosity of 17 cps, and a pH of 7.3 (10% in 50/50 isopropyl alcohol-water).

EXAMPLE II

The procedure described in Example I was repeated except that tetradecylamine was substituted for n-dodecylamine and the reaction product was distilled to provide 96.9% pure clear, water white liquid N-tetradecyl-2-pyrrolidone in a yield of 95% and having a boiling point of 190° C. at 1.0 mm of Hg, a viscosity Of 2 cps, a cloud point (10% $H_2O$ soln.) of 33° C., and a pH (10% in 50/50 isopropyl alcohol-water) of 5.9.

EXAMPLE III

The procedure described in Example I was repeated except that hexadecylamine (Armeen 16D) was substituted for n-dodecylamine and the reaction product was distilled using a hot water condenser and was discharged at about 70° C. to provide 94.5% pure N-hexadecyl-2-pyrrolidone solid in a yield of 90% and having a boiling point of 180° C. at 0.1 m Hg.

EXAMPLE IV

The procedure described in Example I was repeated except that octadecylamine (Armeen 18D) was substituted for n-dodecylamine and the product was stripped of water and excess butyrolactone and was discharged at about 75° C. to provide 96% pure N-octadecyl-2-pyrrolidone solid in a yield of 96%.

EXAMPLE V

The procedure described in Example I is repeated except that eicosylamine is substituted for dodecylamine and the product distilled using a warm water condenser and was discharged at about 85° C. to provide 95% pure N-eicosyl-2-pyrrolidone solid in a yield of about 90%.

EXAMPLE VI

The procedure of Example I was repeated except that Primene 81R (a tertiary $C_{12}$–$C_{14}$ alkyl primary amine) was substituted for n-dodecylamine. The reaction product was distilled to provide 97% pure liquid alkylpyrrolidone product in 40% yield. This product boils at 112°–115° C. at 0.7 mm Hg.

EXAMPLE VII

The procedure described in Example I was repeated except that cocamine distillate was substituted for n-octylamine. The reaction product was stripped of water and excess butryolactone and discharged. The product was obtained in 96% purity and 97% yield.

EXAMPLE VIII

Surface Tension

Surface tension measurements in triplicate were made for each of the N-alkylpyrrolidone species listed below in Table 1, using a Fisher Surface Tensiomat (Model #21, Der Nouy Ring Tensionometer). Each experiment was carried out as follows.

Distilled water solutions at concentrations noted in Table 1 were prepared for each of the following surfactants in 100 ml glass flasks. The solutions were stirred for about 15 minutes until homogeneous solutions were obtained. The surface tensions of these solutions were then measured.

The averaged results of the above tests are reported in Table 1.

TABLE 1

| Surface Tension of Aqueous Solutions at 25° C. (dynes/cm) | | | | | |
|---|---|---|---|---|---|
| | % Solution in Distilled Water | | | | |
| Product | 1.0% | 0.1% | 0.01% | 0.001% | 0.0001% |
| Octyl pyrrolidone | — | 30.4 | 54.25 | 68.4 | — |
| Decyl pyrrolidone | 27.6 | 27.5 | 27.8 | 51.0 | |
| Dodecyl pyrrolidone | — | 26.7 | 27.6 | 29.9 | 55.4 |
| Tetradecyl pyrrolidone | — | 26.4 | 26.5 | 30.4 | 47.5 |

Surface tension data indicates that the N-dodecyl and N-tetradecyl products have particularly strong surface activity, i.e., lowering the surface tension of water.

From the surface tension data, the surface excess concentration $\rho$ (moles/cm$^2$), area/molecule ($a_m$ Å)* at the interface and efficiency of adsorption, (pC$_{20}$)** at the solution/air interface were computed by use of appropriate Gibb's Adsorption Equation:

* Absorption Å$^2$
** The negative logarithm of the surfactant concentration required to lower surface tension by 20 dynes/cm.

$$\rho = \frac{-d\gamma}{d \log c_T} / 2.303 \, RT$$

where $\rho$ = surface excess concentration (moles/cm$^2$)
$d\gamma$ = change in surface or interfacial tension of the solvent $R = 8.31 \times 10$ ergs mol$^{-1}$
c = Molar concentration of solution
T = Absolute Temperature

EXAMPLE IX

The critical micelle concentration (CMC), the surface concentration at the liquid-air interface ($\rho$), the area of the test molecule at the interface (am) and the effectiveness of adsorption at the interface (pC-20) were determined on the above surface tension data reported in Example VIII, Table 1. These properties are reported in Table 2 below.

TABLE 2

| SURFACE ACTIVITY PARAMETERS CALCULATED FROM SURFACE TENSION MEASUREMENTS | | | | |
|---|---|---|---|---|
| Molecule | CMC (ml$^{-1}$) | m (mcm$^{-2}$ × 10$^{10}$) | am (Å)$^2$ | pC-20 |
| N-n-octyl pyrrolidone | — | 4.2 | 39.5 | 3.20 |
| N-n-decyl pyrrolidone | — | 4.6 | 36.1 | 4.51 |
| N-n-dodecyl pyrrolidone | $4.7 \times 10^{-5}$ | 4.5 | 36.9 | 5.27 |
| N-n-tetradecyl pyrrolidone | $5.7 \times 10^{-5}$ | 3.1 | 53.6 | 6.25 |
| lauryl dimethyl amine oxide* | $2.1 \times 10^{-3*}$ | 2.8 | 59.3 | 5.23 |

*Literature value $\rho m = 3.5 \times 10^{-10}$ m cm$^{-1}$, am = 47Å$^2$ (SURFACTANTS AND INTERFACIAL PHENOMENA by Rosen, page 68).

More specifically, the CMC of the N-(n alkyl) pyrrolidones tested show a minimum ($4.7 \times 10^{-5}$) at the $C_{12}$ chain length. Using the empirical equation for n-lauryl ($C_{12}$) alcohol ethoxylate, $$\log C_{CMC} = A^1 + B^1 n$$

where $A^1 = 4.4$, $B^1 = 0.046$, and n = number of ethylene oxide at 23° C., the pyrrolidone ring would be expected to behave as 2 ethylene oxide units. However, the pyrrolidone ring is actually producing results equivalent to about 6 ethylene oxide units, i.e., at 25° C., n-$C_{12}H_{25}$ (ethylene oxide)$_4$ OH (CMC = $4 \times 10^{-5}$) and n-$C_{12}H_{25}$ (ethylene oxide)$_7$ OH (CMC = $5 \times 10^{-5}$). The hydrophilic-lipophilic balance (HLB) of N-n-dodecyl pyrrolidone, based on the assumption that the pyrrolidone ring simulates 2–6 ethylene oxide units is 6.5–11 using the equation % ethylene oxide/5 = HLB. The low apparent HLB suggests the material would be a good water-in-oil emulsifier, e.g., in skin care products.

The surface concentration $\rho$, in moles per cm$^2$ indicates the maximum surface concentration of surfactant, i.e., at equilibrium above the CMC, and is obtained by an estimation of a constant $d\gamma/dc^*$ from the surface tension vs. concentration. The N-(n alkyl) pyrrolidones obtain a maximum Tm ($4.6 \times 10^{-10}$m cm$^{-2}$) at N-$C_{10}H_{21}$ chain length. In general, the Tm for all of the N-n alkyl pyrrolidones is very high in comparison to all, but the less soluble alcohol ethoxylates, i.e., N-$C_{12}H_{25}$ (ethylene oxide)$_4$OH (Tm = $3.8 \times 10^{-10}$m cm$^{-2}$) n-$C_{16}H_{33}$ (ethylene oxide)$_6$OH (Tm = $4.4 \times 10^{-10}$m cm$^{-2}$). The mono disperse nature of the hydrophobe and hydrophile is believed to contribute to high surface concentrations by maximizing enthropy of packing.

* $d\gamma/dc$ = the change in surface tension with respect to the change in surfactant concentration.

EXAMPLE X

Surface tension vs. concentration in the bulk phase at 22° C. was measured (FIG. 1). for aqueous solutions at a pH of 5.8 of N-octyl-2-pyrrolidone, N-decyl-2-pyrrolidone and N-dodecyl-2-pyrrolidone to establish the N-alkyl chain length necessary to form micelles. From the curves of FIG. 1, critical micelle concentrations for compounds are determined.

The aqueous solutions were selected at concentrations about the points of discontinuity (points A, B and C) and absorbance was measured at 600 nm. If precipitation occurs, i.e., no micelle formation, a high variation in absorbance is registered at 600 nm; whereas little or no variation in absorbance shows the formation of the micelle.

The absorbance at 600 nm for aqueous solutions at concentrations about the CMC for the above pyrrolidones are as reported in Table A.

TABLE A

| Wt. % Conc. of N-alkyl-2-pyrrolidone | N-Alkyl*-2-pyrrolidone absorbance at 600 nm | | |
|---|---|---|---|
| | *$C_8$ (Curve C) | *$C_{10}$ (Curve B) | $C_{12}$ (Curve A) |
| 0.0002 | | | 0.004 |
| 0.0005 | | | 0.003 |
| 0.001 | | | 0.003 |
| 0.00115 | | | 0.003 |
| 0.0025 | | | 0.003 |
| 0.005 | | 0.003 | 0.005 |
| 0.007 | | 0.003 | |
| 0.01 | 0.003 | 0.013 | 0.012 |
| 0.012 | 0.003 | | |
| 0.015 | | 0.068 | |
| 0.03 | 0.010 | 0.355 | |
| 0.10 | 0.023 | | |
| 0.15 | 0.163 | | |
| 0.20 | 0.508 | | |

Figure 2:
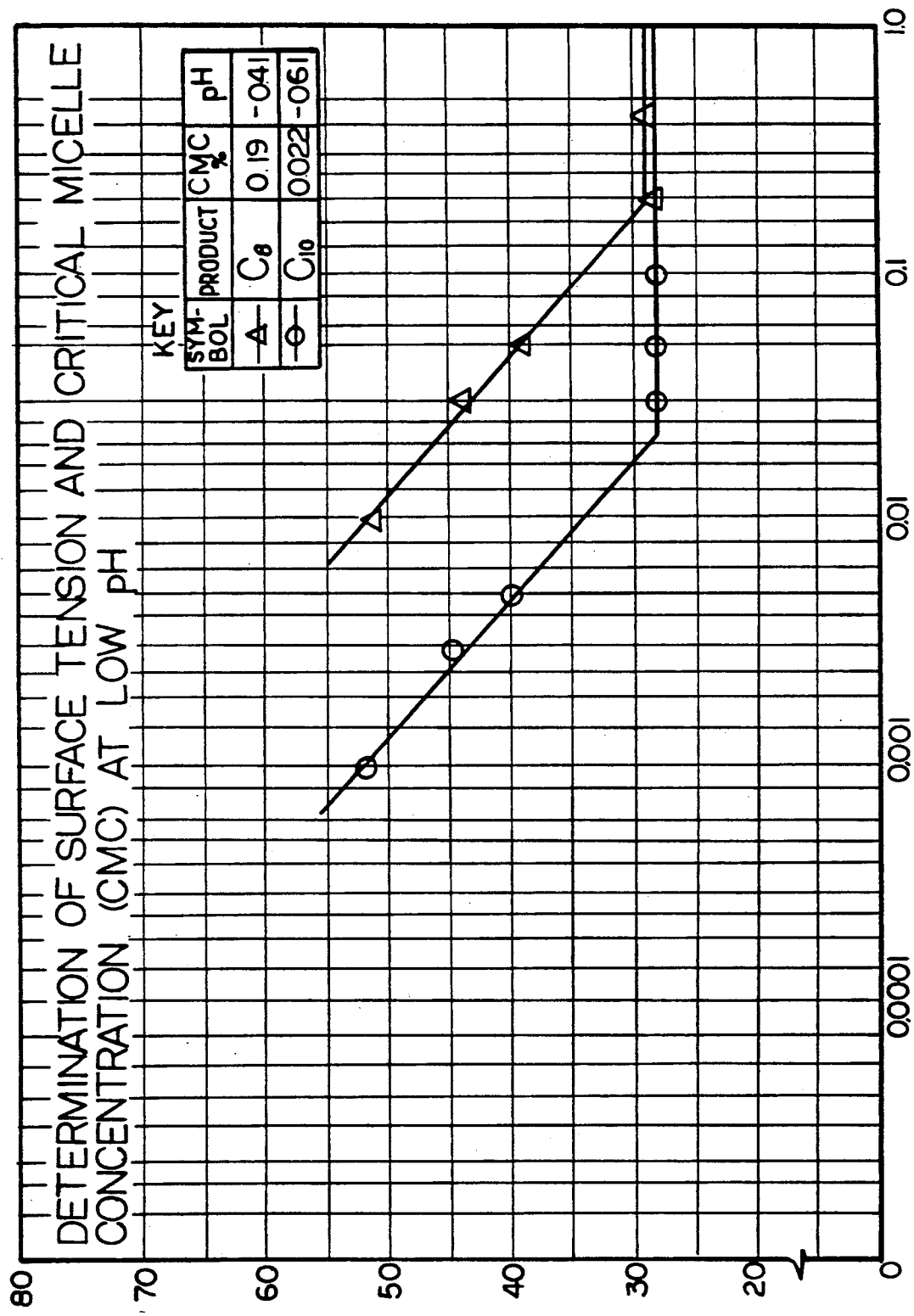
FIG. 2 is a graph similar to that of FIG. 1.

This data indicated a variation in the absorbance at 600 nm for both the $C_8$ and $C_{10}$ compounds. Studies for the $C_{10}$ compound at a pH of 0.61 and for the $C_8$ compound at a pH of 0.41 showed that micelle formation occurs at the CMC of 0.02 and 0.18% by weight, respectively. The aqueous solutions for both of these compounds at the CMC levels showed that the discontinuity of the curves is due to micelle formation rather due to any precipitation of the active material. The results for these tests are shown in FIG. 2.

From the above measurements it was found that N-dodecyl-2-pyrrolidone has a CMC at 0.00115 wt. % or $$\frac{MW \text{ of } C_{12}}{0.00115} \times 10 = 4.5 \times 10^{-5} \text{ moles/liter}$$

As the interface becomes saturated with surfactant molecules, one would expect that within a homologous series, the longer hydrophobic chains would sterically hinder more surfactant molecules from positioning themselves at the interface. The decrease in Tm of the $C_8H_{17}$ vs. the $C_{10}H_{23}$ chain is attributed to the hydrophile/hydrophile interactions of the n-octyl-2-pyrrolidone. Above the $C_{10}H_{23}$ alkyl chain length, normal steric hinderance of the hydrophobes determines Tm.

The area per molecule ($Å^2$) is relative to the Tm, in a comparison of a homologous series. Generally, the area per molecule increases with increasing chain length of the N-(n alkyl) pyrrolidones; however, the larger am of the n-octyl pyrrolidone is attributed to an attraction of pyrrolidone moieties not balanced by the alkyl chain attractions. The low am of the N-(n alkyl) pyrrolidones approaches the theoretical size (20 $Å^2$) for an aliphatic chain oriented perpendicular to the interface.

The negative logarithm of the surfactant concentration required to lower the surface tension by 20 dynes/cm$^{-1}$ can be used as a measure of the efficiency of adsorption since $p$ is approaching the maximum value. The N-(n alkyl) pyrrolidones actually show a progressively higher efficiency of adsorption as the alkyl chain is increased.

EXAMPLE XI

Wetting Test—Drave Method

Into 99.9 ml of distilled water, 0.1% by weight of the N-alkyl-2-pyrrolidone noted in Table 9 was 5 dissolved. The resulting aqueous solution is poured into a one liter glass volumetric flask and 5 g of 100% cotton yarn weighted with a 3 g hook was dropped into the beaker. The time required for the yarn to sink below the surface of the aqueous wetting solution is reported in Table 8. Wetting tests for each of the following N-alkyl-2-pyrrolidone species were run in triplicate.

TABLE 8

| DRAVE'S WETTING DATA AT 25° C. ± 1° C. | |
|---|---|
| Product | Time in Seconds |
| N-Octyl pyrrolidone | 4.4 |
| N-Decyl pyrrolidone | 68.5 |
| N-Dodecyl pyrrolidone | 93.5 |
| N-Tetradecyl pyrrolidone | 109.3 |

The wetting efficacy of the N-n $C_7$ to $C_{20}$ alkyl pyrrolidone series decreases with increasing molecular weight. Of the series, the $C_8$- and probably the $C_7$-alkyl compounds could be considered excellent wetting agents (4.4 seconds wetting at 0.1% for $C_8$-alkyl-2-pyrrolidone).

EXAMPLE XII

Solubility of N-Alkyl Pyrrolidones

Separate 10% by weight solutions of N-alkyl-2-pyrrolidone in the following liquids were made up in 50 ml glass beakers and the solubilities at about 25° C. were noted and reported in following Table 9.

TABLE 9

| | 10% PRODUCT SOLUBILITY AT 25° C. ± 1° C. | | | |
|---|---|---|---|---|
| SOLVENT | N-octyl-2-pyrrolidone | N-decyl-2-pyrrolidone | N-dodecyl-2-pyrrolidone | N-tetradecyl-2-pyrrolidone |
| Water | I | PS* | S* | S* |
| Acetone | S | S | S | S |
| Ethanol | S | S | S | S |
| Xylene | S | S | S | S |
| Heptane | S | S | S | S |
| Paraffin Oil | S | S | PS | S |
| Stoddard Solvent (1) | S** | S | PS | S |
| Perchloroethylene | S | S | S | S |

I = insoluble; PS = partially soluble (cloudy translucent); S = soluble, clear
(1) US Bureau of Standards specification - a clear, water white petroleum distillate
*Soluble with slight haze
**Very slight precipitation The data indicates that alkyl pyrrolidones are soluble in various types of solvents. Although octyl pyrrolidone is insoluble at room temperature in water, decyl pyrrolidone is slightly soluble and dodecyl pyrrolidone and tetradecyl pyrrolidone are completely soluble in water at 10% concentration. However, dodecyl pyrrolidone and tetradecyl pyrrolidone exhibit iridescence phenomena at the 1% to 2% level in aqueous media (violet color at 2% and greenish at about 1%) which was destroyed in the presence of small amount of electrolyte.

It was also observed that 10% aqueous solution of tetradecyl pyrrolidone and dodecyl pyrrolidone become cloudy at about 33°-34° C. and 31°-32° C. respectively exhibiting cloud point phenomena.

The aqueous solubility of the dodecyl and tetradecyl products is interesting, i.e., below 1% (wt. %) solute, the solutions are clear. Between 1 and 2%, the solutions exhibit a scattering pattern (breaks light into its visible spectrum) for visible light indicating a regular geometric pattern which could be regular crystalline spacing (lamellar type) or a monodisperse liquid crystal particle. Above 2%, the solutions again become clear, suggesting a self dissolving effect (loss of regular geometry). This effect once again demonstrates the purity of these compounds. It is postulated that blends of n-alkyl chains would decrease the ability of these materials to form lamellar type structures and increase the aqueous solubility of the less soluble compounds $C_8$ and $C_{10}$). Also it has been observed that low levels of electrolyte eliminate the "prism effects" shown by the 1-2% solutions of the $C_{10}$–$C_{12}$ compounds.

The solubility of the pyrrolidones in both water and in nonpolar solvents such as heptane and perchloroethylene make them useful in nonaqueous applications such as dry cleaning detergents, solubilizers for water in fuels, and cleaners for the removal of solid fatty soil from hard surfaces.

EXAMPLE XIII

The viscosities in cps of the following surfactants at various concentration in distilled water were measured at about 25° C. using a Brookfield Viscometer (LVT Model). The results of these tests are reported in following Table 10.

TABLE 10

| PRODUCT | VISCOSITY (CPS) AT VARIOUS WEIGHT % WATER CONCENTRATIONS | | | | | |
|---|---|---|---|---|---|---|
| | 100% | 10% | 8% | 6% | 4% | 2% |
| N-octyl-2-pyrrolidone | 8.0 | — | — | — | — | — |
| N-decyl-2-pyrrolidone | 12.0 | — | — | — | — | — |
| N-dodecyl-2-pyrrolidone | 17.0 | 20.0 | 16.0 | 12.5 | 7.5 | 6.5 |
| N-tetradecyl-2-pyrrolidone | 20.0 | 145.0 | 100.0 | 96.0 | 66.0 | 24.5 |
| Ammonyx LO | — | 7.0 | — | — | — | 4.0 |
| Ammonyx MO | — | 52.5 | — | — | — | 7.0 |
| Control (distilled water) | 1.0 | — | — | — | — | — |

The above viscosity of alkyl pyrrolidones and their aqueous solutions were obtained using a #2 spindle at a speed of 30 rpm, and a #2 spindle at a speed of 60 rpm respectively.

Data indicates that viscosity of the (100% active) alkyl pyrrolidone increased as the carbon chain length of alkyl group increased.

Both tetradecyl and dodecyl pyrrolidone exhibit a significant thickening increase. The higher viscosities of the N-n alkyl pyrrolidones vs. dimethyl fatty amine oxides of similar chain length indicate that the micelles of the N-n alkyl pyrrolidones are lamellar or rod shaped as compared to spherical types for the amine oxides.

EXAMPLE XIV

Viscosity Building

Several samples to be tested were prepared in 1500 ml glass beakers by mixing 47.9 wt. % of deionized water at 60° C. with 50 wt. % surfactant and 0.6 wt. % of the viscosity builder (100% active) to be tested while agitating constantly with an electric stirrer. The resulting solution was allowed to cool to 40° C. whereupon 0.05 wt. % of Kathon CG preservative was added with stirring and the solution allowed to cool to room temperature A control solution was prepared for each surfactant used in the same manner except that viscosity builder was omitted from the control formulations and 49.95 wt. % of deionized water was employed.

The viscosity was measured in cps for each of the above solutions by adding 20% NaCl solution from a glass pipette in 2 ml increments until the Peak viscosity break point was reached. Anhydrous sodium chloride was used when requirements exceeded 4% NaCl by weight. The results of these tests which report the viscosity at the break point for each test solution and for each control are reported in the following Table 11.

TABLE 11

| | VISCOSITY (CPS) |
|---|---|
| SURFACTANT = Na lauryl sulfate | |
| Viscosity Builder | |
| N-dodecyl-2-pyrrolidone | 12,285 |
| coconut diethanol amide | 13,000 |
| lauryl dimethylamine oxide | 10,140 |
| cocamidopropyl betaine | 17,850 |
| cocamidopropyl hydroxy sultaine | 12,425 |
| Control | 1,850 |
| SURFACTANT = Na laureth sulfate (3 moles ethylene oxide) | |
| Viscosity Builder | |
| N-dodecyl-2-pyrrolidone | 40,000 |
| coconut diethanol amide | 36,820 |
| lauryl dimethylene oxide | 31,590 |
| cocamidopropyl betaine | 55,680 |
| cocamidopropyl hydroxy sultaine | 54,540 |
| Control | 30,000 |
| SURFACTANT = Ammonium lauryl sulfate | |
| Viscosity Builder | |
| N-dodecyl-2-pyrrolidone | 40,000 |
| coconut diethanol amide | 33,200 |
| lauryl dimethylamine oxide | 37,270 |
| cocamidopropyl betaine | 54,590 |
| cocamidopropyl hydroxy sultaine | 28,180 |
| Control | 6,360 |

EXAMPLE XV

Protonation of N-n Alkyl Pyrrolidones to Form Cations

The cation formed by protonation of N-dodecyl pyrrolidone, i.e.,

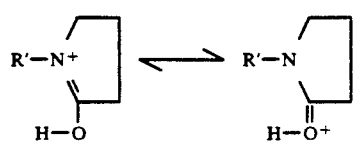

was precipitated from acid solution using a large anionic surfactant molecule, linear dodecyl benzene sulfonate.

Both the $C_8$ and $C_{10}$ alkyl pyrrolidones which are rather insoluble in water at pH 7, are readily solubilized in acid solution. Ten percent dispersions of the $C_8$ and $C_{10}$ pyrrolidones were titrated to a clear solution using HCl. The results are shown in the following table, Table 12.

TABLE 12

MOLAR RATIO OF HCl TO ALKYL PYRROLIDONE REQUIRED FOR SOLUBILIZATION

| N-n-alkyl group | Grams of Pyrrolidone (10% Dispersion) | HCl (ml.) 36.7% | Mole Ratio HCl/ Pyrrolidone | Solution pH |
|---|---|---|---|---|
| octyl | 20.0 | 5.2 | 6.2 | 0.22 |
| decyl | 20.0 | 9.7 | 12.8 | <0.1 |

To obtain a rough figure for the protonation equilibrium constant, the equilibrium [octyl pyrrolidone] was taken at $5 \times 10^{-3}$. Additionally, the specific gravity of the 10% dispersion was taken at 1.0 g/cc. Calculation indicates that $K = 1.3 \times 10^2$ for the octyl pyrrolidone forming a cation, i.e., [octyl pyrrolidone]+[H*]⇌[protonated pyrrolidone]*.

Solubility of the present surfactants in highly alkaline solutions is limited and the pyrrolidone ring is not hydrolyzed in such environments. However the solubility in acid is very high. Data indicate that the present N-alkyl-2-pyrrolidones are much less prone to acid hydrolysis than N-methyl pyrrolidone. Mixtures (50/50) of the N-n alkyl pyrrolidones with 36.7% HCl were made. The $C_8$ and $C_{10}$ alkyl pyrrolidones were clear, viscous liquids at 25° C., while the $C_{12}$ alkyl/HCl mix was a homogeneous, transparent gel. The $C_{14}$/HCl (50/50) mixture became a non-homogeneous solid at room temperature.

EXAMPLE XVI

The density at 25° C., heat of vaporization in kilocalorie per mole and solubility parameter was determined for the $C_8$, $C_{10}$, $C_{12}$ and $C_{14}$ alkyl pyrrolidone species of the invention. These parameters are reported in following Table 14.

TABLE 14

| PRODUCT | $d_{25°}$ C. | Heat of Vaporization k cal/mole | Solubility Parameter (δ) |
|---|---|---|---|
| N-n-octyl-2-pyrrolidone | 0.920 | 15.0 | 8.2 |
| N-n-decyl-2-pyrrolidone | 0.911 | 18.4 | 8.5 |
| N-n-dodecyl-2-pyrrolidone | 0.903 | 18.0 | 7.9 |
| N-n-tetradecyl-2-pyrrolidone | 0.896 | 19.7 | 7.8 |

The present compounds possess dye transfer properties which permit better penetration of a dye into a cellulosic substrate. Accordingly, the present compounds are useful vehicles for dyeing or printing.

EXAMPLE XVII

A 50% black dye formulation of 1:1.5 triarylmethane dye portion of C.I. Basic Blue and a methine dye portion of C.I. Basic Violet 16, C.I. Basic Yellow 29 and C.I. Basic Orange 21, dissolved in an aqueous vehicle containing 20 wt. % of N-dodecyl-2-pyrrolidone provides improved penetration of the dye into a swatch of white orlon fabric at room temperature and high exhaustion of dye on the fabric.

Other representative formulations which suitably employ the products of this invention are presented below, although these are by no means limiting to the scope of suitable mixtures. The following formulations and compositions are prepared by conventional methods and require no detailed description. Generally the components are mixed at between about room temperature and about 100° C. under ambient pressure until a uniform composition is obtained. Addition of the present lactams to any of the numerous commercial detergent and/or disinfectant solutions materially enhances their cleaning and sanitizing properties. The effective amount of lactam preferably employed ranges from about 0.2% to about 20% by volume of the total composition. The following formulations are representative.

| A. Standard Dishwashing Compositions | Vol. % |
|---|---|
| (i) Water | 59.4 |
| Ethanol (95%) | 8.6 |
| Alfonic 1412-A (59.3% (ethylene oxide sulfate) | 22.5 |
| Alfonic 1412-10 (linear alcohol ethoxylate) | 1.1 |
| Sodium Chloride | .9 |
| N-decyl-2-pyrrolidone | 7.5 |
| | % by Wt. |
| (ii) Sulfated nonylphenoxypoly (ethyleneoxy) Ethanol ammonium salt | 9.00 |
| Cocamide diethanol amide | 2.50 |
| Ethoxylated nonylohenol (10 Mol EO) | 8.00 |
| Nonylphenyl sulfonate (60%) | 20.00 |
| Sodium xylene sulfonate (40%) | 9.00 |
| 50/50 mixture of N-n-octyl- and N-n-dodecyl-2-pyrrolidones | 3.00 |
| Fragrance | 0.25 |
| H$_2$O | 48.25 |

| B. Machine Dishwashing Liquid | % by Wt. |
|---|---|
| Tetrasodium pyrophosphate | 22.00 |
| Sodium metasilicate | 10.00 |
| Sodium benzoate | 1.00 |
| Sodium xylene sulfonate (40%) | 1.00 |
| Glycol ether | 2.00 |
| Capryloamphocarboxy glycinate | 6.00 |
| 50/50 mixture of N-n-octyl- and N-n-dodecyl-2-pyrrolidones | 3.00 |
| Fragrance | 0.50 |
| H$_2$O | 54.50 |

| C. Bottle Washing Composition Useful in pressure bottle washing equipment | % by Wt. |
|---|---|
| Cocoamphocarboxypropionate | 1.00 |
| Carbitol solvent (an alkyl ether of diethylene glycol) | 1.00 |
| Sodium Hydroxide (flakes) | 20.00 |
| N-dodecyl-2-pyrrolidone | 5.00 |
| Water | 73.00 |

| D. General purpose Liquid Glass Cleaner | % by Wt. |
|---|---|
| Glycol ether (Arcosolve DPM) | 4.00 |
| Ammonium Hydroxide (28%) | 1.00 |
| Polyoxyethylene/polyoxypropylene block copolymer | 0.10 |
| N-n-Octyl-2-pyrrolidone | 1.00 |
| Fragrance | Q.S. |
| Water | to 100 % |

| E. Fine Fabric Washing Detergent | % by Wt. |
|---|---|
| Linear decyl benzene sulfonate | 5.00 |
| Coconut diethanolamide | 20.00 |
| Sodium lauryl ether sulfate (3 mol EO) | 15.00 |
| Sodium xylene sulfonate (40%) | 10.00 |
| Citric Acid | to pH 7 |
| Preservative | Q.S. |
| Colorant | Q.S. |
| N-n-dodecyl-2-pyrrolidone | 5.00 |
| Water | to 100 % |

Formulation E is particularly suited for woolen and nylon fabrics. The low surface tension of the pyrrolidone component permits high detergent action through the nap of knitted fabrics.

| F. Cold Water phosphated Laundry Detergent | % by Wt. |
|---|---|
| Sodium tripolyphosphate | 50.0 |
| Sodium silicate (2:1 ratio) | 10.0 |
| Sodium sulfate | 17.5 |
| N-$C_8$-$C_{16}$ alkyl-2-pyrrolidone mixture | 17.5 |
| $H_2O$ | 5.0 |

Grimy dirt and greasy sebum was easily removed by one cycle washing (15 min + 5 min rinse) with the above formulation at 80° F. The test was conducted in 120 ppm water hardness.

| G. Hard Surface Cleaners | | % by Wt. |
|---|---|---|
| (i) | Tetrasodium phosphate | 0.70 |
| | Sodium metasilicate -$5H_2O$ | 0.50 |
| | n-dodecyl benzene sulfonate | 1.13 |
| | N-n-octyl-2-pyrrolidone | 0.75 |
| | Sodium xylene sulfonate | 6.80 |
| | $H_2O$ | 90.12 |

The improved cleaning capacity of this formulation is attributed to the co-surfactant function of n-octyl pyrrolidone with n-dodecyl benzene sulfonate.

| | | % by Wt. |
|---|---|---|
| (ii) | Sodium lauryl ether sulfate (3 Mol EO) | 20.00 |
| | Coconut diethanolamide | 10.00 |
| | Ethylene glycol monobutyl ether | 5.00 |
| | Tetrasodium ethylene diamine tetraacetic acid (EDTA) | 1.00 |
| | 50/50 mixture of N-n-octyl- and N-n-dodecyl-2-pyrrolidones | 3.00 |
| | Fragrance | Q.S. |
| | Preservative | Q.S. |
| | Colorant | Q.S. |
| | Water | to 100% |
| H. Disinfectant; Sanitizing & Decontaminating Detergents | | |
| (i) | Bardac 205M (octyldecyl dimethyl benzyl ammonium chloride) | 2.80 |
| | N-dodecyl-2-Pyrrolidone | 1.20 |
| | $H_2O$ | 96.00 |
| (ii) | Miranol C 2M-SF (dicarboxylic coconut derivative sodium salt, amphoteric) | 15.00 |
| | Quaternary ammonium salt, 50% (Decyldimethyl octyl ammonium chloride) | 2.00 |
| | Sodium carbonate | 2.00 |
| | Ethylene tetraacetic acid | 0.50 |
| | N-n-dodecyl-2-pyrrolidone | 0.50 |
| | $H_2O$ | 80.00 |
| (iii) | Benzalkonium chloride | 5.00 |
| | Sodium carbonate | 2.00 |
| | Sodium citrate | 1.50 |
| | Nonoxynol 10 (10 av. ethoxylated nonyl phenol) | 2.50 |
| | N-n-octyl-2-pyrrolidone | 5.00 |
| | $H_2O$ | 84.00 |
| (iv) | Lauric/myristic diethanolamide | 7.00 |
| | Sodium lauryl sulfate | 6.00 |
| | Trisodium phosphate | 2.00 |
| | Sodium tripolyphosphate | 2.00 |
| | N-n-octyl-2-pyrrolidone | 5.00 |
| | Fragrance | 0.50 |
| | $H_2O$ | 77.50 |
| (v) | Magnesium aluminum silicate | 0.90 |
| | Kelzan gum thickener | 0.45 |
| | tetrasodium EDTA | 1.00 |
| | Monazoline-O*/Imidazoline | 1.00 |
| | Hydrochloric acid (37%) | 20.00 |
| | Barquat MB-80 (alkyl dimethyl benzyl ammonium chloride) | 1.25 |
| | 50/50 mixture of N-n-octyl- and N-n-dodecyl-2-pyrrolidones | 3.00 |
| | Fragrance (acid stable) | 1.00 |
| | $H_2O$ | 71.40 |

*substituted imidazoline of oleic acid

The formulations H-(i) through H-(v) are particularly suited for hospital and institutional use in washing porcelain tile, tubs, toilet bowls, sinks, shower stalls, etc., associated fixtures and floors. They are also effective cleaning liquids which reduce or eliminate animal odors as may be encountered in a veterinarian hospital or doctor's office or in the home, since the N-alkyl lactam possesses the property of complexing with urea and mercapto type compounds. For odor masking effects somewhat higher amounts of the pyrrolidone component, e.g., up to about 10% of the formulation, may be employed, if desired.

| I. General Purpose Medium Duty Liquid Alkaline Cleaner | % by Wt. |
|---|---|
| Sodium hydroxide (50%) | 1.00 |
| Potassium hydroxide (45%) | 1.50 |
| Sodium metasilicate (anhydrous) | 2.50 |
| Sodium tri-polyphosphate | 3.00 |
| Nitrilotriacetic acid | 3.00 |
| Monateric CEM-38 (Coconut amphoteric surfactant) | 2.00 |
| Monafax 831 (a Phosphate ester) | 1.00 |
| 50/50 mixture of N-n-octyl- and N-n-dodecyl-2-pyrrolidones | 3.00 |
| Fragrance | 0.50 |
| $H_2O$ | 82.50 |

Formulation I is particularly useful for cleaning metal surfaces, ceramic tile and household appliances.

| | % by Wt. |
|---|---|
| J. Dairy Equipment Liquid Cleaner | |
| Gluconic Acid (50%) | 20.00 |
| Sodium Nonoxynol -9 phosphate* | 10.00 |
| N-n-octyl-2-pyrrolidone | 5.00 |
| $H_2O$ | 65.00 |
| K. Liquid Rug Shampoo | |
| Sipex 7WC concentrate (blend of ionic and nonionic surfactants, $C_{12}$ av. chain length) | 10.00 |
| Lauryl ether sulfate (3 mole EO) | 10.00 |
| Sodium tripolyphosphate | 2.00 |
| Ethyl carbitol solvent | 1.50 |
| Tinopal 5BM optical brightener (diamino stilbene) | 0.05 |
| N-n-dodecyl-2-pyrrolidone | 2.00 |
| Fragrance | Q.S. |
| Preservative | Q.S. |
| $H_2O$ | to 100% |

*the sodium phosphate of 9 av. ethyoxylated nonyl phenol

The complexing properties of the pyrrolidone component, as explained in the formulations H-(i) through H-(v), enable the shampoo formulation to eliminate pet odors as well as providing superior cleaning and depositing a microfilm of pyrrolidone which acts as a barrier against redeposit of soil.

| L. Fabric Softener | % by Wt. |
|---|---|
| Miranol DM (monocarboxylic stearic derivative, sodium salt) | 3.00 |
| Arquad 2HT 75-(dimethyl [hydrogenated tallow] ammonium chloride) | 2.00 |

| L. Fabric Softener | % by Wt. |
|---|---|
| N-n-dodecyl-2-pyrrolidone | 1.00 |
| Fragrance | 0.25 |
| H$_2$O | 93.75 |

Formulation L can be added directly to the washing detergent or used to impregnate non-woven strips employed in a clothes dryer or sprayed directly on fabric after laundering.

| M. Antistat formulations | % by Wt. |
|---|---|
| (wash cycle additive) | |
| (i) Sodium silicate (2:1 ratio SiO$_2$ to Na$_2$O) | 10.00 |
| Lauric acid | 0.20 |
| Sodium hydroxide | 0.20 |
| Sodium carbonate | 33.25 |
| Sodium sulfate | 43.20 |
| (1) Igepal CO-630 | 7.00 |
| N-n-dodecylpyrrolidone | 5.00 |
| H$_2$O | 1.15 |

(1) 100% active liquid condensation product of nonyl alcohol and nine units of ethylene oxide The above formulation significantly lowered the static electricity on clothes dried in an automatic dryer and is compatible with wash cycle detergents.
(ii) Melted polypropylene having a melt flow index of 8 and a density of 0.902 at 200° C. was mixed with 1% by weight of N-dodecyl-2-pyrrolidone and extruded from a twin screw extruder to form bottles. The same operation was repeated with the melted polypropylene, but omitting the 1% pyrrolidone. Unlike the pyrrolidone deficient composition, those bottles containing pyrrolidone did not pick up dust or lint after 10 passes over a nylon cloth and their surface resistivity was measured at $1\times10^{12}$ ohm at 30% humidity, as opposed to $4\times10^{14}$ ohm (30% humidity) reported for the pyrrolidone deficient polypropylene bottles.

| N. Liquid Softening/Antistat Composition | % by Wt. |
|---|---|
| N-n-tetradecylpyrrolidone | 5.4 |
| (2) Igepal CO-660 | 23.9 |
| H$_2$O | 55.7 |
| Ethanol | 15.0 |

(2) 100% active liquid/liquid condensation product of nonyl alcohol and ten units of ethylene oxide The above formulation exhibited the same properties as Formulation C.

Anti-static compositions incorporating from about 5% to about 100% of the present lactams as the active ingredient are also usefully applied as aerosol sprays to rugs, clothing and furniture whereby the anionic charges accumulated on these surfaces are neutralized and discharged by the mildly cationic character of the present lactams below pH 7.

| O. Complexed Compositions | % by Wt. |
|---|---|
| H$_2$O | 60.99 |
| N-n-dodecylpyrrolidone | 10.48 |
| Sodium iodide | 22.20 |
| Iodine | 6.33 |

The N-n-dodecyl pyrrolidone-iodine micelle complex (iodophor) which formed provides improved iodine solubility for disinfecting purposes.

| P. Acid thickener | % by Wt. |
|---|---|
| Concentrated HCl | 50.0 |
| N-n-dodecylpyrrolidone | 50.0 |

The H* complexation of the N-n-dodecyl pyrrolidone with the acid significantly increased the acid viscosity so that the formulation can be applied to vertical surfaces without runoff and can be employed for other uses without splattering.

| Q. Perfume | Parts by Wt. |
|---|---|
| Lilac | 80 |
| Muguet | 5 |
| 3% Musk extract | 5 |
| Tuberose absolute | 2 |
| Jasmine | 8 |
| 90% alcohol | 800 |
| N-pentadecyl-2-pyrrolidone or N-tetradecyl-2-pyrrolidone | 100 |

Retention of the perfume odor on the skin is remarkably extended.

| R. | Dry Cleaning Formulations | % by Wt. |
|---|---|---|
| (i) | Perchloroethylene | 94.50 |
| | Isopropyl methyl cellulose | 0.50 |
| | N-tetradecyl-2-pyrrolidone | 5.00 |
| (ii) | Perchloroethylene | 46.00 |
| | Ethoxylated nonylphenol phosphate ester (GAFAC RS-610 and PF-510, 2:1) | 31.00 |
| | N-hexadecyl-2-pyrrolidone | 15.00 |
| | Potassium hydroxide | 8.00 |
| (iii) | Stoddard solvent (a petroleum distillate between gasoline & kerosene) | 41.50 |
| | GAFAC RS-610 | 30.00 |
| | Nekal WT-27 (sulfonated aliphatic polyester) | 7.50 |
| | Hexylene glycol | 10.00 |
| | Potassium hydroxide | 8.00 |
| | N-dodecyl-2-pyrrolidone | 3.00 |
| (iv) | Perchloroethylene | 40.00 |
| | Isopropanol | 5.00 |
| | N-dodecyl-2-pyrrolidone | 50.00 |
| | Water | 5.00 |

The above formulations are highly effective in removal of wine, tea, fruit and other water soluble and oil soluble stains together with normal soil. Additionally, the present lactams eliminate any perspiration stains or body odor remaining in a fabric.

The above and many other formulations which require one or more of the properties imparted by the present pyrrolidone products are suitably employed in the present invention. Also, any of the N-C$_7$ to C$_{22}$ alkyl-caprolactams can be substituted therein to provide those benefits described for the alkyl pyrrolidones.

| S. Formulation for Industrial Odor Control | % by Wt. |
|---|---|
| N-octyl-2-pyrrolidone | 2.00 |
| Dodecylbenzene sulfonic acid | 5.00 |
| Sodium xylene sulfonate | 2.00 |
| Ethoxylated (av.9) nonylpheno | 15.00 |
| H$_2$O | to 100% |

Formulation S was sprayed at a rate of 1 lb./cubic yard over the soil in which odoriferous lauryl mercaptan had been accidentally spilled. After 1 hour, the objectionable odor was completely eliminated.

| T. Removing Rug Shampoo | % by Wt. |
|---|---|
| Sodium lauryl sulfate | 12.00 |
| N-dodecyl-2-pyrrolidone | 3.00 |
| Sodium xylene sulfonate | 2.00 |
| H$_2$O | to 100% |

Formulation T was applied to a new rug which had been soiled by dog urine and strong amine/mercaptan odor. After drying, the stain and odor of treated rug was reduced to the mildest trace. The application can be repeated for complete odor removal. The omission of pyrrolidone in the above formulation has no odor removing effect whatever when applied to another portion of the rug soiled in the same manner.

EXAMPLE XVIII

In a glass round bottom 100 ml flask equipped with a thermometer and a condenser was added 24.34 g (0.1 mole) of N-dodecyl-2-pyrrolidone and 11.1 g (0.1 mole) hydroquinone. The mixture was heated and stirred until a homogeneous liquid phase was obtained. The melt was maintained at about 135° C. for 30 minutes, whereupon it was chilled to about 20° C. The crystalline solid product which formed had an m.p. of 78°-82° C. The complex structure was evidenced by IR spectra which showed a shift of the pyrrolidone carbonyl from 1692 CM$^{-1}$ to 1654 CM$^{-1}$ and 1612 CM$^{-1}$. Proton nuclear magnetic resonance ('HNMR) at 25°±2° C. indicated a 1:1 molar complex.

EXAMPLE XIX

Example XXVIII is repeated except that only 12.17 g (0.05 mole) of N-dodecyl-2-pyrrolidone is used and 13.32 g (0.05 mole) of pentachlorophenol is substituted for 11.1 g of hydroquinone and the resulting melt is heated at 120° C. for 30 minutes. A solid crystalline micellular complex of 1:1 molar N-dodecyl-2-pyrrolidone/pentachlorophenol is formed.

EXAMPLE XX

Example XXIX is repeated except that 7.61 g (0.05 mole) of vanillin was substituted for 13.32 g of pentachlorophenol. The mixture was heated until homogeneous and was then maintained at 60° C. for 30 minutes. A low melting crystalline micellular complex was formed.

EXAMPLE XXI

In an NMR tube, a mixture of 0.1 molar N-dodecyl-2-pyrrolidone and different concentrations of phenol, from 0.1 to 0.3M, was dissolved in deuterated chloroform and analyzed by 300 megahertz 'HNMR at 25°±2° C. In each case, the phenolic OH shifted to higher frequency in the presence of N-dodecyl-2-pyrrolidone which shows complexation of N-dodecyl-2-pyrrolidone and phenol through intermolecular hydrogen bonding.

EXAMPLE XXII

To 200 g of beer is added 50 g of N-n-dodecyl-2-pyrrolidone with stirring until a uniform mixture is obtained and the mixture is cooled to 15°-20° C. to provide a clear solution. The solution is then heated to 25° C. whereupon two liquid phases are formed and separated.

The clear beer fraction, which is the lower phase, is recovered and analyzed by the method of J. Jerumanis (Brauwissenschaft Vol. 25, #10, pages 319-321. Analysis shows that 90% of the phenolic impurities are complexed with dodecyl pyrrolidone efficiently removed.

EXAMPLE XXIII

A 2×2 inch swatch of white 100% cotton was impregnated with blue black ink in a 0.5 inch circular area. The swatch was then held under hot water while rubbing for 1 minute. A barely noticeable amount of the ink was removed. The swatch was then placed on a clean counter and 1 drop of 100% N-n-dodecyl-2-pyrrolidone from a medicine dropper was contacted with the ink spot, and allowed to remain for 1 minute; after which the swatch was held under warm water while rubbing for 0.5 minute. The sample was then dried and examined for ink removal. Only the faintest shadow of a barely discernable blue color remained.

The above experiment was repeated except that 100% N-n-octyl-2-pyrrolidone was substituted for N-n-dodecyl-2-pyrrolidone. Dye removal was even more complete so that magnification was needed to detect color.

The above compounds can be employed individually or in admixture and used as the sole spot removing agent for home or commercial laundering or in a dry cleaning operation. The compounds may also be incorporated into a commercial stain and spot removing formulation to boost stain removing properties.

EXAMPLE XXIV

To improve the dissolution rate of hydrochlorothiazide tablets, the blend:

|  | % by Wt. | Per tablet |
|---|---|---|
| Hydrochlorothiazide | 10.0 | 45.00 mg |
| N-octyl-2-pyrrolidone | 0.5 | 2.25 mg |
| 1:1 mixture of lactose: dicalcium phosphate | 88.5 | 398.25 mg |
| Magnesium stearate | 1.0 | 4.50 mg | was prepared by blending the hydrochlorothiazide with an ethanolic solution of the N-octyl-pyrrolidone and dried in an oven at 60° C. The dried material was blended with the lactose/dicalcium phosphate diluent for 7 minutes, after which the magnesium stearate lubricant was added and mixed for an additional 3 minutes. The resulting material was then compressed into tablets of 8-10 Kp hardness by using a Stokes B-2 tablet press.

The above procedure was repeated except that the addition of N-octyl pyrrolidone was omitted to provide a control formulation.

Finally the above procedure was again repeated, except that the conventional sodium lauryl sulfate surfactant was substituted for the N-octyl-pyrrolidone surfactant to provide a standard against which the efficacy of the present lactam was measured.

Figure 3:
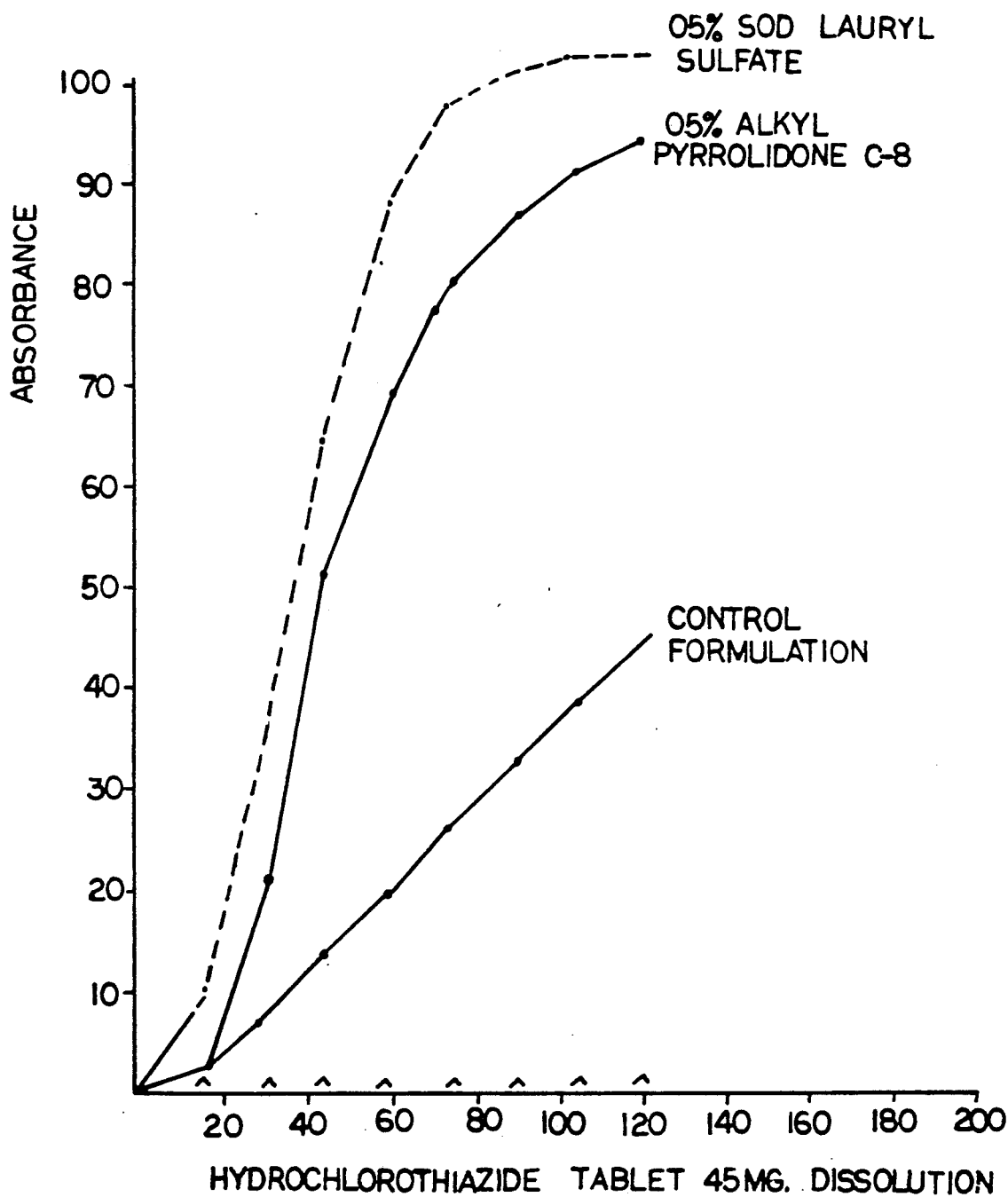
FIG. 3 is a graph showing the variation in absorbance with time for different hydrochlorothiazide compositions.

The dissolution of hydrochlorothiazide was then measured using a PharmaTest dissolution apparatus and dissolution method 711 as disclosed in the USP XX, page 378. The dissolution was followed by measuring the UV absorbance at Λ272 nm. Six measurements for each sample were obtained. The average of one six were then plotted versus time and this plot is depicted in FIG. 3.

The N-octyl pyrrolidone significantly enhanced the dissolution rate of the drug from a directly compressible system and proved to be almost as effective as sodium lauryl sulfate while superior in other properties such as its non-irritability and non reactivity with acidic drugs and pharmaceutical excipients. It is well known that sodium lauryl sulfate is highly irritating and its alkaline character causes it to react with acidic components which leads to compatibility problems as well as problems with the physical characteristics of the finished products.

The above procedure for preparing Sample B was twice repeated except that 0.1% by weight and 0.5% by weight of N-dodecyl-2-pyrrolidone was substituted for 0.5% by wt of N-octyl-2-pyrrolidone and the balance of the formulation was taken up by the diluent (Samples E and F respectively).

The dissolution rates were measured, the results of which are reported in following Table I.

TABLE I

| Sample | % Dissolution of Drug | | | |
|---|---|---|---|---|
| | After 30 min | After 60 min | After 90 min | After 120 min |
| E (0.1% NDP) | 9.63 | 27.24 | 49.64 | 67.64 |
| F (0.5% NDP) | 19.92 | 59.11 | 87.07 | 96.20 |

The procedure for preparing Sample B was repeated 4 times except that 0.5 wt % of N-decyl-2-pyrrolidone (Sample G); 0.5 wt % of N-tetradecyl-2-pyrrolidone (Sample H); 0.5 wt % of N-octadecyl-2-pyrrolidone (Sample I) and 0.5 wt % of N-methyl-2-pyrrolidone (Sample J) were substituted for 0.5 wt % of N-octyl-2-pyrrolidone. The dissolution rates for these pyrrolidones were measured, the results of which are reported in Table II.

TABLE II

| Sample | After 30 min | After 60 min | After 90 min | After 120 min |
|---|---|---|---|---|
| G | 19.26 | 51.18 | 78.15 | 96.09 |
| H | 19.15 | 61.81 | 87.40 | 92.52 |
| I | 6.60 | 19.92 | 34.78 | 50.63 |
| J | 6.49 | 16.51 | 26.97 | 39.19 |
| Control | 7.93 | 20.80 | 33.46 | 44.80 |

The above results indicate that all of the pyrrolidones tested significantly increased the drug dissolution rate over that of the control; however, the results achieved with N-octyl pyrrolidone were outstanding and $C_{10}$ to $C_{14}$ alkyl pyrrolidones were only slightly less effective. The dissolution rate increasing effect falls off markedly with the $C_{18}$ a alkyl pyrrolidone and is virtually non-existent in the lower molecular weight solvent type pyrrolidones which lack surfactant properties.

EXAMPLE XXV

To improve the dissolution rate of chlorothiazide tablets, the following blends were made up:

| | | % by Wt. |
|---|---|---|
| K | Chlorothiazide | 10.00 |
| | N-dodecyl-2-pyrrolidone | 0.50 |
| | 1:1 mixture of lactose:dicalcium phosphate | 88.50 |
| | Magnesium stearate | 1.00 |
| L | Chlorothiazide | 10.00 |
| | N-dodecyl-2-pyrrolidone | 0.25 |
| | 1:1 mixture of lactose:dicalcium phosphate | 88.75 |
| | Magnesium stearate | 1.00 |
| M | Chlorothiazide | 10.00 |
| | N-dodecyl-2-pyrrolidone | 0.10 |
| | 1:1 mixture of lactose:dicalcium phosphate | 88.90 |

-continued

| | | % by Wt. |
|---|---|---|
| | Magnesium stearate | 1.00 |
| N | Chlorothiazide | 10.00 |
| | 1:1 mixture of lactose:dicalcium phosphate | 99.00 |
| | Magnesium stearate | 1.00 |

Blends K-M were prepared by mixing the chlorothiazide with an ethanolic solution of N-dodecyl-2-pyrrolidone and dried in an oven at 60° C. The dried material was blended with the lactose/dicalcium phosphate diluent for 7 minutes, after which the magnesium stearate was added and mixed for an additional 3 minutes. The resulting blends were then compressed into tablets of 8-10 Kp hardness and the dissolution of chlorothiazide was measured for each of K, L and M as reported in Table IV.

The blend of Sample N was similarly prepared except that N-dodecyl-2-pyrrolidone was omitted. This sample served as a control.

TABLE III

| Sample | After 60 min. | After 120 min. | After 180 min. |
|---|---|---|---|
| K | 49.14 | 90.24 | 99.26 |
| L | 58.06 | 96.33 | 103.29 |
| M | 13.48 | 23.81 | 56.54 |
| N | 16.63 | 24.79 | 31.09 |

Figure 4:
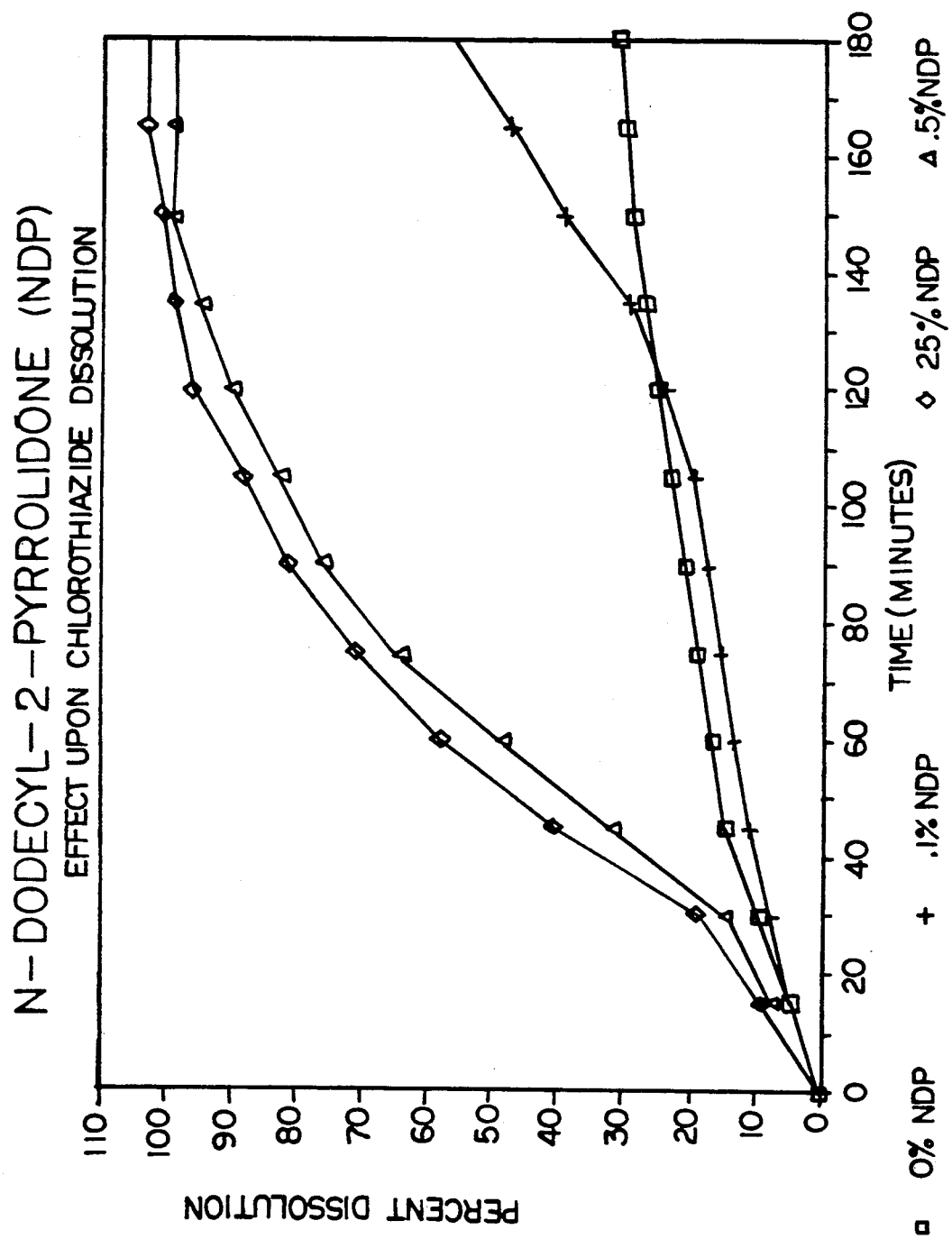
FIG. 4 is a graph showing the variation in dissolution with time of chlorothiazide compositions containing different amounts of N-dodecyl-2-pyrrolidone.

The above data indicates the enhancement dissolution properties of N-dodecyl-2-pyrrolidone when employed in the above blends at a concentration of at least 0.25% by weight. Even at the 0.1 wt % concentration level, some improvement was noted after 3 hours. This data is shown graphically in FIG. 4.

EXAMPLE XXVI

Demonstration of Slip and Antiblock Properties 1,000 ppm of N-dodecyl-2-pyrrolidone was mixed into molten polypropylene having a melt flow index 8 and a density of 0.902 at 200° C. The resulting melt was conducted through an in-line mixer to an extruder from which a 1 mil blown film was deposited on a clean stainless steel surface. The above procedure was repeated, except that the pyrrolidone was omitted. The coefficients of friction for the films were measured and the pyrrolidone containing film indicated a significant reduction compared to the untreated film. This reduction or "slip" development reaches a maximum within 24 hours, indicating rapid blooming of the pyrrolidone to the film surface. The following Table IV summarized the data.

TABLE IV

| Coefficient of Friction: Cast Polypropylene Film | | | |
|---|---|---|---|
| Elapsed Time Hours | Untreated Polypropylene | Film containing N—$C_{12}$-pyrrolidone (1,000 ppm) | Film containing Kemamide E (Erucamide) (1,000 ppm) |
| 1 | 1.2 | 0.50 | 0.73 |
| 3 | 1.2 | 0.38 | 0.65 |
| 6 | 1.2 | 0.25 | 0.61 |
| 24 | 1.2 | 0.21 | 0.48 |
| 48 | 1.2 | 0.21 | 0.44 |

The data indicates the superior utility of the N-dodecyl pyrrolidone in the above melt.

EXAMPLE XXVII

Demonstration of Dye Enhancing Properties

A low density polyethylene having a melt index 8 at 200° C. was mixed with 0.5% by weight N-dodecyl-2-pyrrolidone. The resulting uniform mixture was transferred to an extruder from which clothes-hangers were produced. The procedure was repeated except that mixture with a pyrrolidone was omitted. Unlike the untreated polymer, the N-dodecyl-2-pyrrolidone containing thermoplastic absorbed 0.1% cationic dye having an anionic charge, (CI Acid Yellow 49), from boiling water upon immersion for one hour.

No absorption occurred with the pyrrolidone deficient melt. Other suitable acid anionic dyes which are beneficially absorbed by the lactams of this invention include CI Acid Blue 40, Cl Acid Red 337, Cl Acid Yellow 159, Cl Acid Yellow 79 and CI Acid Yellow 151.

The following examples illustrates a low-energy process for removing organic pollutants from aqueous streams in waste water treatment. The waste waters included within the scope of this invention are sewage, wastes from industrial processes, such as for example a pulp paper mill, chemicals manufacture, plastic manufacturing, dairy and food processing; industrial spills of fuel oil and other contaminating chemicals and power plant waste waters. Of particular interest are the phenolic, halogen, mercapto, sulfur dioxide, nitric oxide and urea type contaminants contained in such waste waters.

Phenolic compounds are specially troublesome because, not only are they widely used in a great number of applications ranging from agricultural chemicals to food additives but also because they are unavoidably formed in many industrial processes. Phenolics are known to impart a disagreeable taste and odor to drinking water and edible aquatic life forms and are believed to be harmful against man and/or the environment. However, current methods for phenolic decontamination are time-consuming and laborious. The present low energy process provides an efficient method for removing these contaminants.

EXAMPLE XXVIII

Aqueous 100 ml solutions of the following phenolics were prepared in 1 liter glass flasks. To these aqueous solutions was added N-octyl-2-pyrrolidone in the amounts indicated in Table VI. After the addition, the contents of the flasks were allowed to stand for 15 to 30 minutes, whereupon two liquid layers separated, i.e., an upper organic layer containing phenolics and N-octyl-2-pyrrolidone and a lower water layer. The layers were separated and weighed for phenolic content which was determined by UV absorption.

TABLE VI

| Sample Soln. | Grams of phenolic in Water | % N—$C_8$ P added to soln. | Grams of Phenolic in Separated Lactam Soln. | % phenolic Separated Lactam |
|---|---|---|---|---|
| 1 | 0.02 g. Phenol | 2 | 0.02 | >90 |
| 2 | 0.02 g. 2,4-di-methyl Phenol | 2 | 0.02 | >90 |
| 3 | 0.03 g. Penta-chloro Phenol | 2 | 0.03 | >90 |

EXAMPLE XXIX

A 50 ml. deionized water sample containing an organophosphorous salt, namely a 1:1 ratio of dialkyl phosphate and tetraphenyl arsenic chloride salt was contacted with 4 ml. of N-octyl-2-pyrrolidone. After completion of the addition, the resulting mixture was allowed to stand for 15 minutes at room temperature; whereupon 2 layers separated: a lower water layer and an upper pyrrolidone layer. Analysis showed that the separated pyrrolidone layer contained more than 80% of the organophosphorous salt compound.

Where the above experiment is repeated with N-dodecyl-2-pyrrolidone or N-tetradecyl-2-pyrrolidone, a micellular complex is formed with the tetraphenyl arsenic chloride and 85% of the organophosphorous salt is removed from water.

It is to be understood that the foregoing examples are merely representative and serve to illustrate the diverse properties discovered for the present lactams. Because of the multifarious effects of the present lactams, many more applications, modifications and alterations than specifically disclosed in the foregoing specification will become apparent to those skilled in the art. These are also within the scope of this invention. Particularly included are substitutions of any of the lactams disclosed herein in any of the above formulations and examples and any particular applications which derive from the unique properties of the present group of lactams including their complexability, surfactant properties, viscosity building, foam stabilizing, and surface tension reducing properties.

What is claimed is:

1. A composition comprising an N-hydrocarbon-substituted lactam having the formula

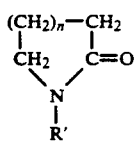

wherein n is an integer having a value of from 1 to 3 and R' is a hydrophobic radical consisting of a linear, branched chain or cyclic alkyl radical containing from 12 to 22 carbon atoms; a naphthyl or alkyl substituted naphthyl radical containing from 10 to 26 carbon atoms and an alkylphenyl or phenylalkyl radical containing from 9 to 26 carbon atoms; which lactams are capable of forming micelles in neutral, basic or acidic aqueous media and have a critical micelle concentration of between about $1 \times 10^{-3}$ and about $5 \times 10^{-5}$ moles per liter and a phenolic compound.

2. The composition of claim 1 wherein said phenolic compound is hydroquinone, or a halogenated phenol.

* * * * *